United States Patent [19]

Nesti

[11] Patent Number: 4,807,617
[45] Date of Patent: Feb. 28, 1989

[54] SCAVENGING MASK

[75] Inventor: William Nesti, Brockton, Mass.

[73] Assignee: Massachusetts Eye and Ear Infirmary, Boston, Mass.

[21] Appl. No.: 150,774

[22] Filed: Feb. 1, 1988

[51] Int. Cl.$^4$ .................. A62B 18/02; A62B 18/08
[52] U.S. Cl. .................. 128/205.12; 128/910; 128/206.28; 128/205.25; 128/203.29
[58] Field of Search .............. 128/910, 203.12, 204.26, 128/205.12, 205.24, 205.25, 206.12, 206.17, 207.18, 207.13, 202.27, 205.19, 206.16, 206.21, 206.27, 206.28

[56] References Cited

U.S. PATENT DOCUMENTS

| 2,248,477 | 7/1941 | Lombard | 128/205.25 |
|---|---|---|---|
| 3,721,239 | 3/1973 | Myers | 128/188 |
| 3,815,596 | 6/1974 | Keener et al. | 128/188 |
| 3,901,230 | 8/1975 | Henkin | 128/188 |
| 3,960,148 | 6/1976 | Dryden | 128/188 |
| 4,015,598 | 4/1977 | Brown | 128/188 |
| 4,109,651 | 8/1978 | Steingerwald | 128/145 |
| 4,151,843 | 5/1979 | Brekke et al. | 128/203 |
| 4,219,020 | 8/1980 | Czajka | 128/207 |
| 4,248,218 | 2/1981 | Fischer | 128/204 |
| 4,249,528 | 2/1981 | Mathes | 128/205 |
| 4,265,239 | 5/1981 | Fischer, Jr. et al. | 128/205 |
| 4,312,339 | 1/1982 | Thompson, Sr. | 128/205 |
| 4,332,244 | 6/1982 | Levy et al. | 128/205 |
| 4,337,767 | 7/1982 | Yahata | 128/206.28 |
| 4,527,558 | 7/1985 | Hoenig | 128/205 |
| 4,538,605 | 9/1985 | Gedeon et al. | 128/205 |
| 4,565,196 | 1/1986 | Melby et al. | 128/205 |
| 4,653,493 | 3/1987 | Hoppough | 128/202 |

FOREIGN PATENT DOCUMENTS 3331374 3/1985 Fed. Rep. of Germany .................. 128/203.12

Primary Examiner—Edgar S. Burr
Assistant Examiner—Kimberly L. Asher

[57] ABSTRACT

Removable apparatus suitable for scavenging gas from the vicinity of a gas delivery mask applied to a face. The mask has a convex outer surface, and the apparatus comprises a cup having an inner concave surface adapted to form a gap between it and the convex surface of the mask when the cup is positioned over the mask. The cup is adapted so as not to contact the face when positioned over the mask when the mask is placed over the face. Also provided is an aperture in the cup for allowing evacuation of the gas from the gap.

10 Claims, 3 Drawing Sheets

SCAVENGING MASK

BACKGROUND OF THE INVENTION

This invention concerns apparatus for scavenging anesthetic gas from around a mask.

Fischer, Jr. et al. (U.S. Pat. No. 4,265,239; 1981) describes a mask having an exhaust assembly for removing exhaled gases. This assembly also has a peripheral exhaust chamber for scavenging gases leaking from the mask.

Brown (U.S. Pat. No. 4,015,598; 1977) describes an anesthetic mask for collecting gases exhaled by a patient and gases leaking from the mask. The mask has an inner shell connected by a pressure relief valve to an outer shell. Gases in the outer shell are removed by an exhaust pump. The outer shell is open at its lower surface to scavenge gases which leak from the mask.

Czajka (U.S. Pat. No. 4,219,020; 1980) describes a scavenging attachment which replaces the exhalation valve of a conventional face mask. The attachment has a floating disc check valve connected to a generally concave inverted saucer-shaped vacuum chamber. Gas leaking around the periphery of the mask is scavenged by a vacuum connected to this chamber. Exhaled gases are also removed by a vacuum system connected to this chamber.

Gedeon et al. (U.S. Pat. No. 4,538,605; 1985) describe an apparatus having a pressure activated valve which regulates the operation of a suction device on a gas mask. When the valve is turned on all gas entering the mask is sucked away by the device.

Hoenig (U.S. Pat. No. 4,527,558; 1985) describes a scavenging system in which all gases exhaled by a patient are collected in a manifold and then sucked away by a vacuum system.

Fischer (U.S. Pat. No. 4,248,218; 1981) describes an apparatus for administering gas via nasal cannulae. These cannulae are surrounded by a mask connected to a vacuum system which removes exhaled gases. Gases exhaled through the mouth are scavenged through this mask via apertures in its base.

SUMMARY OF THE INVENTION

In a first aspect, the invention features a removable apparatus, and method for its use, suitable for scavenging gas from the vicinity of a gas delivery mask applied to a face. The mask has a convex outer surface and the apparatus includes a cup, having an inner concave surface adapted to form a gap between it and the convex surface of the mask, when the cup is positioned over the mask. Further, the cup is adapted so as not to contact the face of a patient when the cup is positioned over the mask and when the mask is placed over the face. Also provided is an aperture in the cup for allowing evacuation of gas from the gap.

In preferred embodiments, the cup is generally an inverted boat-shaped cup; the cup has a second aperture for the passage therethrough of a gas supply tube on the mask; the cup has at its perimeter a flange which cooperates with the mask to form the gap; and the cup is transparent.

In a related aspect, the invention features a kit including a gas delivery mask and the above-described removable apparatus. Preferably the kit further includes spacer means e.g., a washer, for separating the cup and mask to form the gap.

The apparatus is used by providing a gas delivery mask and the above apparatus. The method further includes positioning the apparatus over the mask, and connecting a vacuum source with the apparatus.

This invention provides an inexpensive disposable attachment for standard gas delivery masks. Because it fits over a standard mask, and can be connected with a standard vacuum supply in an operating room, no extra equipment need be purchased by the user. The attachment can be constructed from clear plastic, thus allowing the anesthesiologist to observe the patient's face continuously, and providing a less frightening mask for young children, compared with the heavy opaque masks currently available.

Other features and advantages of the invention will be apparent from the following description of the preferred embodiments thereof, and from the claims.

DESCRIPTION OF THE PREFERRED EMBODIMENT

We first briefly describe the drawings.

Drawings

Figure 1:
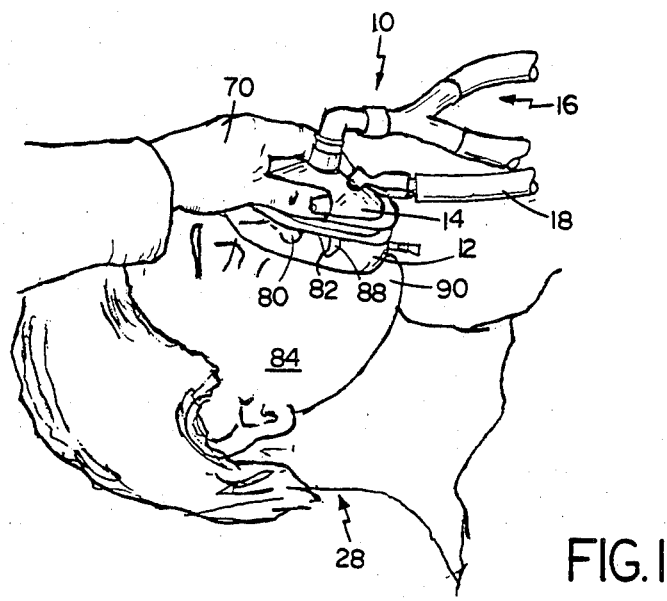

FIG. 1 is a perspective view of a gas delivery mask and scavenging attachment of the invention in use.

Figure 2:
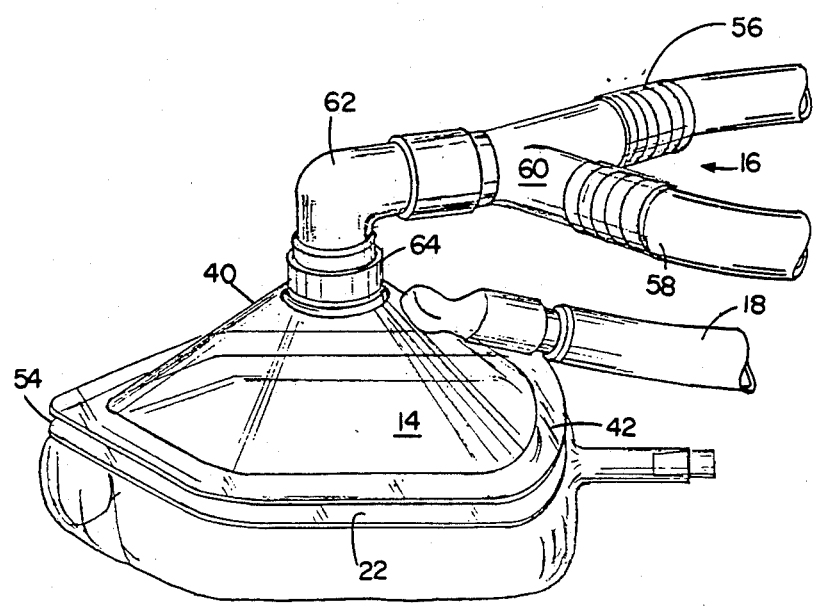
Figure 3:
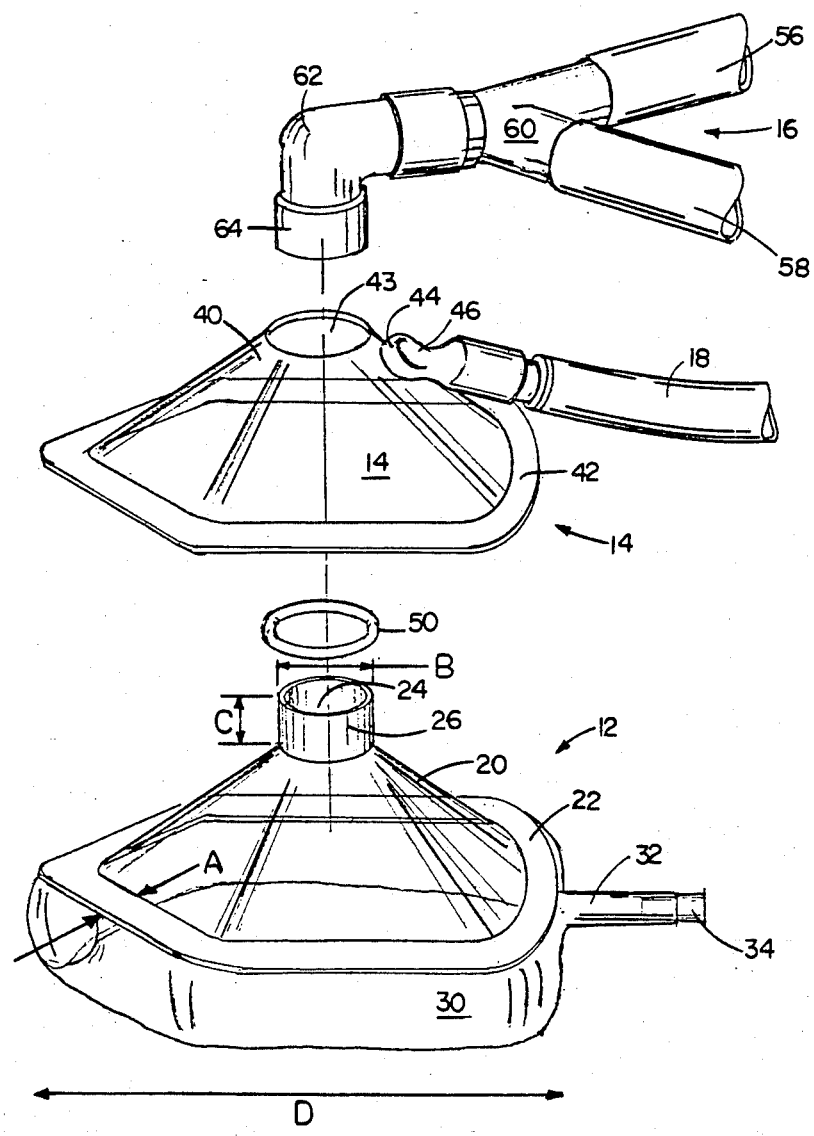
Figure 4:
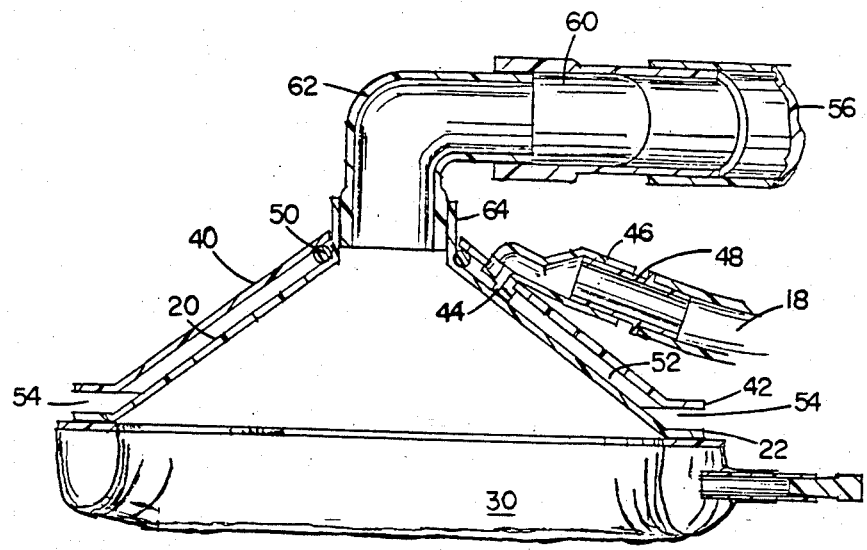

FIGS. 2, 3, and 4 are a perspective view, an exploded perspective view, and a longitudinal cross-sectional view, respectively, of a gas delivery mask and a scavenging attachment.

Figure 5:
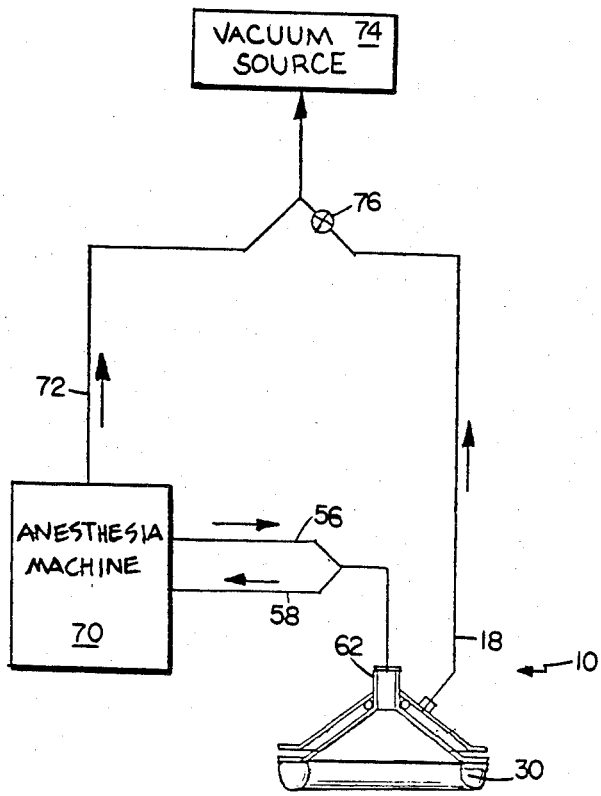

FIG. 5 is a diagrammatic illustration of the gas lead connections for a face mask and scavenging attachment.

Structure

Referring to FIGS. 1-4, mask assembly 10 is provided with a standard gas delivery mask 12, a scavenging attachment 14, gas supply and exhalation hoses 16, and vacuum hose 18.

Mask 12 is constructed from a generally concave inverted boat shaped cup 20 having a generally horizontal perimeter flange 22 of width A, about ⅜", and a centrally located aperture 24 at the end of a short conical tube 26 of internal diameter B about ¾", external diameter about 1", and length C, about ¾". The length, D, of cup 20 is sufficient to be placed over the mouth and nose of a patient 28, about 5". Attached below flange 22, by adhesive, is an airtight inflatable flexible tube 30 formed from clear polymeric plastic of about 1¼" diameter. A short tube 32 is also provided, to allow inflation of tube 30, and a plug 34 to maintain tube 30 in an inflated condition.

Scavenging attachment 14 is also constructed from a generally concave inverted boat shaped cup 40 having a generally horizontal perimeter flange 42 of dimensions as described above for cup 20. Cup 40 has a centrally located aperture 43 of diameter about 1" through which tube 26 can be inserted. Also provided is a second aperture 44 connected to an adapter 46 for connection with vacuum hose 18 using connecting tube 48. Between scavenging attachment 14 and mask 12 is a washer 50 of internal diameter about 1", designed to fit snugly over tube 26. Washer 50 acts as a spacer between cups 20 and 40 to form a gap 52 having an outer perimeter gap 54. Gap 54 has a height of about ¼".

Gas supply hose 56 and exhalation hose 58 are connected by a Y-connector 60 to a right angle tube 62 having a lower end 64, of outer diameter about ¾", which fits snugly within tube 26.

Manufacture

Cups 20 and 40 are both formed from a clear hard plastic, and tube 30 of a flexible clear plastic. Hoses 16, 18, and their connections are formed from a suitable clear plastic material.

Assembly

Referring to FIG. 3, mask 12 is prepared for use by first inflating tube 30 to a sufficient extent to provide tight comfortable contact with a patient's face. This tube is then sealed with plug 34. Washer 50 is placed over tube 26 and then scavenging attachment 14 placed such that cups 20 and 40 overlay each other with tube 26 inserted through aperture 43. Right angle tube 62 is then inserted over tube 64 and hoses 56, 58, and 18 attached as appropriate.

Referring to FIG. 5, exhalation and gas supply hoses 56, 58 are connected by standard procedure to anesthetic machine 70, which in turn has a scavenging hose 72 connected to a standard operating room vacuum source 74. Vacuum hose 18 is also connected to standard vacuum source 74. A tap 76 is provided in hose 18 to allow disconnection of the vacuum supply as required.

Use

Referring to FIG. 1, during use both face mask 12 and scavenging attachment 14 cover nose 80 and mouth 82 of a patient 28 to be anesthetized. The point of contact between mask 12 and face 84 is airtight inflatable flexible tube 30. When tube 30 is inflated to a relatively low pressure (relative to ambient pressure), sealed, and mask 12 placed on face 84, tube 30 conforms to the contours of face 84 and provides a comfortably fitting gas barrier. Tube 30 contacts the face between lower lip 88 and chin 90, extends along the side of mouth 82 and nose 80, and then above the bridge of nose 80.

Anesthetic gases are delivered by standard procedure to face mask 12 via hose 56 and Y-fitting 60. Gases expelled by the patient are withdrawn through Y-fitting 60 and line 58 to anesthesia machine 70.

Assembly 10 is held in place over patient 28 by one hand 90 of an anethesiologist. The mouth and nose of patient 28 are visible through the assembly so that any problems, e.g., vomiting, can be readily observed.

When a vacuum source is connected to hose 18 gas within gaps 52 and 54 is removed. Gap 54 is closed at the point of contact of washer 50 and cups 20 and 40 and thus gases from around perimeter gap 54 are sucked up through gaps 54 and 52 into vacuum hose 18. In this way anesthetic gases leaking from around tube 30 are rapidly removed from air in the operating room.

It is preferable to provide each of the above described components as a kit with each component separately sterilized.

Other embodiments are within the following claims. For example, cups 20 and 40 may be separated by molded protrusions on their surfaces, rather than by use of a washer; such protrusions will act to allow a gap to be formed between the inner and outer surfaces of these cups.

I claim:

1. A removable apparatus usable with a succession of gas delivery masks, for scavenging gas from the vicinity of a gas delivery mask applied to a face, said mask having a convex outer surface, a discrete gas supply means and a discrete gas exhaust means, and being operable alone as a gas delivery mask, said apparatus comprising a cup having an inner concave surface adapted to form a gap between it and the convex surface of said gas delivery mask when said cup is positioned over said gas delivery mask, said cup being shaped so as not to contact said face when positioned over said gas delivery mask when said gas delivery mask is placed over said face, said cup further comprising an aperture adapted for attachment to a gas scavenging line, separate and discrete from said gas exhaust means, for allowing evacuation of gas from said gap, wherein said apparatus is a discrete unit, being readily removable from said gas delivery mask and capable of being used with a succession of gas delivery masks.

2. The apparatus of claim 1 further comprising a second aperture for the passage therethrough of a gas supply tube for connection to said mask.

3. The apparatus of claim 1 wherein said cup has at its perimeter a flange which cooperates with said mask to form said gap.

4. The apparatus of claim 1 wherein said cup is transparent.

5. A kit comprising a gas delivery mask and the removable apparatus of claim 1.

6. The kit of claim 5, further comprising a spacer means for separating said cup and said mask to form said gap.

7. A method for scavenging gas from the vicinity of a gas delivery mask including the steps of:
providing said gas delivery mask having a convex outer surface, a discrete gas supply means and a discrete gas exhaust means, and operable alone as a gas delivery mask,
applying said gas delivery mask to a patient's face,
providing a removable apparatus suitable for scavenging gas from the vicinity of the gas delivery mask applied to a face,
in the form of a cup having an inner concave surface adapted to form a gap between it and the convex surface of said gas delivery mask when said cup is positioned over said gas delivery mask, said cup being shaped so as not to contact said face when positioned over said gas delivery mask when said gas delivery mask is placed over said face, said cup further comprising an aperture adapted for attachment to a gas scavenging line, separate and discrete from said gas exhaust means, for allowing evacuation of said gas from said gap, wherein said apparatus is a discrete unit, being readily removable from said gas delivery mask and capable of being used with a succession of gas delivery masks,
positioning said apparatus over said gas delivery mask,
connecting a vacuum source to said apparatus, and
removing gas from said gap through said aperture.

8. A disposable face mask assembly comprising a discrete gas delivery mask operable alone as a gas delivery system, having a discrete gas supply means and a discrete gas exhaust means, and a discrete scavenging attachment having an aperture adapted for attachment to a gas scavenging line, separate and discrete from said gas exhaust means, capable of being used with a succession of gas delivery masks, wherein when said attachment is placed over said gas delivery mask a gap is formed between said gas delivery mask and said attachment, and wherein gases can be removed from said gap by connecting a vacuum line to said attachment.

9. The assembly of claim 8, wherein said attachment is adapted for insertion over the gas supply tube of said mask.

10. The assembly of claim 9, wherein said attachment is held in place over said mask by the tube supplying gases to said mask.

* * * * *